(12) United States Patent
Spahn

(10) Patent No.: US 7,399,974 B2
(45) Date of Patent: Jul. 15, 2008

(54) METHOD, CORRECTION METHOD AND X-RAY SYSTEM

(75) Inventor: Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/657,010

(22) Filed: Jan. 24, 2007

(65) Prior Publication Data

US 2007/0183571 A1   Aug. 9, 2007

(30) Foreign Application Priority Data

Jan. 25, 2006   (DE) .................... 10 2006 003 612

(51) Int. Cl.
*G01J 1/24* (2006.01)
*H05G 1/64* (2006.01)

(52) U.S. Cl. .................... 250/370.09; 378/98

(58) Field of Classification Search ............ 250/370.08, 250/370.09, 370.11; 378/62, 98
See application file for complete search history.

(56) References Cited

U.S. PATENT DOCUMENTS 5,604,781 A   2/1997   Suzuki

2002/0195567 A1   12/2002   Spivak

FOREIGN PATENT DOCUMENTS

| DE | 196 04 631 A1 | 8/1996 |
| DE | 199 49 792 A1 | 4/2001 |
| DE | 10 2004 003 881 A1 | 7/2005 |

OTHER PUBLICATIONS

German Office Action.

*Primary Examiner*—David P. Porta
*Assistant Examiner*—Faye Boosalis
(74) *Attorney, Agent, or Firm*—Harness, Dickey & Pierce, P.L.C.

(57) ABSTRACT

For improved temperature-dependent correction, a method is provided for compiling a temperature-adjusted correction image for the electronic correction of a raw X-ray image recorded by an X-ray detector at a recording temperature. In at least one embodiment, the temperature-adjusted correction image, in particular the temperature-adjusted gain correction image, is generated by numerical calculation from at least one correction image which was recorded at a temperature differing from the recording temperature. In the event of a difference between the recording temperature and the temperature or temperatures for which recorded correction images are available, the raw X-ray image is corrected electronically by use of the temperature-adjusted correction image.

21 Claims, 5 Drawing Sheets

METHOD, CORRECTION METHOD AND X-RAY SYSTEM

PRIORITY STATEMENT

The present application hereby claims priority under 35 U.S.C. §119 on German patent application number DE 10 2006 003 612.3 filed Jan. 25, 2006, the entire contents of which is hereby incorporated herein by reference.

FIELD

Embodiments of the invention generally relate to a method for compiling a temperature-adjusted correction image, to a correction method, to a method for generating a corrected X-ray image and/or to an X-ray system.

BACKGROUND

Image amplifier camera systems which are based on television or CCD cameras, storage film systems with an integrated or external readout unit, systems with optical coupling of a converter film to CCD cameras or CMOS chips, selenium-based detectors with electrostatic readout and X-ray detectors, in particular flat image detectors, having an active readout matrix with direct or indirect conversion of the X-radiation are known in digital X-ray imaging.

Such a detector is based on an active readout matrix, for example one or more detector plates made of amorphous silicon (a-Si) which is coated on the front with an X-ray converter layer or a scintillator layer. The active matrix is subdivided into a multiplicity of pixel readout units. In a so-called directly converting X-ray detector, the incident X-radiation is converted directly into electrical charge in the converter layer. In an indirectly converting X-ray detector, the incident X-radiation is converted into visible light in the scintillator and then in turn converted into electrical charge in photodiodes of the active matrix. This charge can then be stored in the pixel readout units and read out; the resulting raw X-ray images may subsequently be post-processed.

In order to obtain high-quality X-ray images, some of the effects due to the specific properties of the respective X-ray detector need to be corrected electronically. The most important electronic corrections are offset corrections in which the dark current is corrected, and gain corrections which compensate for sensitivity variations of the X-ray detector. In general offset corrections are carried out by electronic subtraction, and gain corrections by electronic multiplication with previously compiled offset or gain calibration images.

Overall the combined offset and gain correction, the so-called flat field correction, can generally be described in the following way:

$$K = G \cdot [S-O] \text{ or } K_i = G_i \cdot [S_i - O_i],$$

where S represents the raw X-ray image and $S_i$ the raw value relating to the respective pixel readout element i, O represents the offset correction image and $O_i$ the offset value, G represents the gain correction image and $G_i$ the gain value, K represents the corrected X-ray image and $K_i$ the corrected final value.

Temperature changes of the X-ray detector generally lead to offset structures and sensitivity differences, above all in edge and transition regions of the active matrix of the X-ray converter. The latter may, for example, occur by temperature-related expansion or contraction of layers. If calibration images are recorded at a different temperature than the raw X-ray images, then false corrections often occur.

It is known from DE 10 2004 003 881 A1 to monitor the temperature of an X-ray detector and record a new calibration image in the event of a substantial temperature rise of the X-ray detector.

It is however often not possible to record a calibration image matching each X-ray recording, in particular a gain calibration image, rather it is necessary to resort to gain calibration images already recorded. These have generally been recorded at temperatures differing from the exact recording temperature.

SUMMARY

In at least one embodiment of the invention, a temperature-dependent correction of a raw X-ray image as and when required, is improved.

At least one embodiment of the invention is based on the idea, in the event of a difference between the recording temperature and the temperature or temperatures for which correction images are available, of generating a correction image temperature-adjusted to the recording temperature by numerical calculation from the latter and thereby providing a possibility for exactly correcting a raw X-ray image.

Correspondingly, an electronic correction of the respective raw X-ray image can be carried out by way of the temperature-adjusted correction image generated by numerical calculation, so that a corrected X-ray image can be obtained with a particularly small or even no correction error and with a temperature-independent high image quality.

At least one embodiment is particularly advantageous for gain correction images, since large differences between the recording temperature of the gain correction image and that of the raw X-ray image can lead to strong artifacts after the correction. The alternative, i.e. to record a gain correction image at the same recording temperature for each raw X-ray image, would entail great outlay. The invention is not however restricted to gain correction images; rather it also covers other correction images, for example offset correction images or defect correction images.

At least one embodiment of the invention offers great advantages, particularly for X-ray detectors in which strong temperature variations can occur, for example in portable X-ray detectors, uncooled equipment or X-ray detectors which switch between an energy saving mode and an active mode.

For a particularly good correction possibility of the raw X-ray image, which also entails little outlay, the temperature adjusted correction image is advantageously generated from at least two correction images recorded at different temperatures. For particularly straightforward generation of the temperature-adjusted correction image in this context, it is advantageous to generate it by interpolation, in particular linear interpolation.

According to one configuration of at least one embodiment of the invention, the temperature-adjusted correction image is generated by extrapolation, in particular linear extrapolation.

According to another configuration of at least one embodiment of the invention, the temperature-adjusted correction image is generated by numerical calculation from at least one correction image which was recorded at a temperature differing from the recording temperature, while incorporating a physical property of the X-ray detector or while incorporating a physical property of parts of the X-ray detector. In this way, a temperature-adjusted correction is possible even when only a single correction image recorded at a temperature differing from the recording temperature is available.

For a particularly exact calculation, the temperature-adjusted correction image is calculated numerically while taking into account a temperature-induced volume change, in particular an expansion, of the X-ray detector or while taking into account a temperature-induced volume change, in particular an expansion, of subcomponents of the X-ray detector.

According to another configuration of at least one embodiment of the invention, physical coefficients, in particular expansion coefficients, of the X-ray detector or of subcomponents of the X-ray detector are used. Expediently, in particular the expansion coefficients of the scintillator layer and of a substrate material of the X-ray detector are used.

According to another configuration of at least one embodiment of the invention, the volume change is assumed to be axisymmetric with respect to the center of a detector plate of the X-ray detector.

According to at least one embodiment of the invention, in the event of a substantial difference between the recording temperature and the temperature or temperatures for which correction images are available, a temperature-adjusted correction image may be generated by way of a method according to at least one embodiment of the invention and the raw X-ray image may subsequently be corrected electronically by way of the temperature-adjusted correction image; if correction images are already available, however, which were recorded at a temperature equal or at least similar to the recording temperature or have been generated by way of a calibration method, then the correction images already available are advantageously used for electronically correcting the raw X-ray image. In this context a substantial difference refers to a difference which, for example, leads to a false correction intolerable for a user; this will vary depending on the application.

In order to carry out a particularly exact electronic correction of a raw X-ray image, an X-ray system according to at least one embodiment of the invention is provided having an X-ray detector and an image processing unit for compiling a corrected X-ray image, wherein the X-ray detector includes a temperature sensor and is designed to record a raw X-ray image at a recording temperature, and wherein the image processing unit is designed to generate a temperature-adjusted correction image by numerical calculation from at least one correction image recorded at a temperature differing from the recording temperature and to correct the raw X-ray image electronically with the temperature-adjusted correction image.

BRIEF DESCRIPTION OF THE DRAWINGS

Embodiments of the invention and further advantageous configurations will be explained in more detail below with the aid of schematically represented example embodiments in the drawings, without thereby restricting the invention to these example embodiments.

DETAILED DESCRIPTION OF THE EXAMPLE EMBODIMENTS

Figure 1:
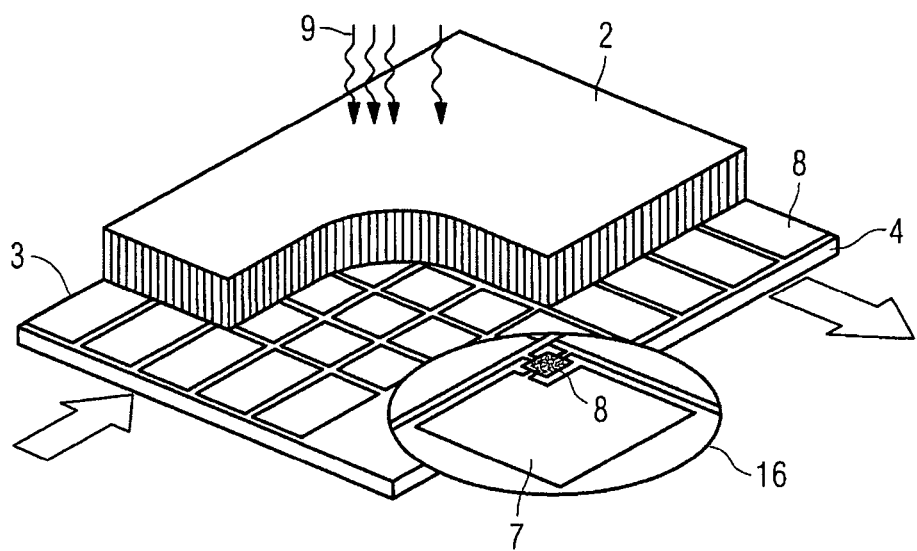
FIG. 1 shows a perspective view of a digital X-ray detector designed as a flat image detector.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 2:
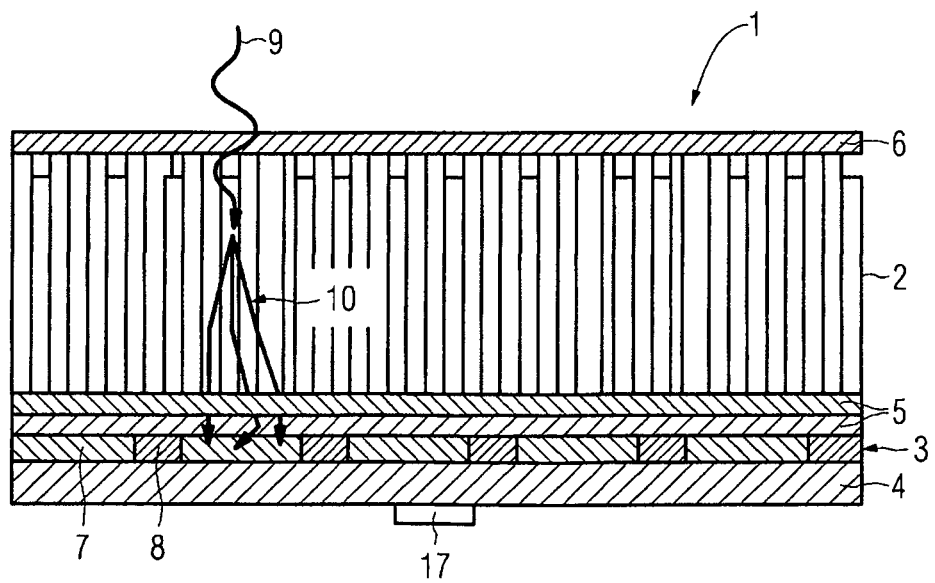
FIG. 2 shows a side view through a digital X-ray detector designed as a flat image detector.

FIG. 1 and FIG. 2 show an example of a digital X-ray detector 1, designed as a flat image detector, in perspective view and as a section. As essential components, the X-ray detector 1 includes a scintillator layer 2, an active matrix including an a-Si plate 3 with pixel readout elements 16 and a substrate 4 carrying the active matrix. The a-Si plate 3 is formed by a multiplicity of pixel readout elements 16, each of which is in turn divided into a photodiode 7 and a switching element 8 (Thin Film Transistor=TFT). A scintillator carrier 6 is generally arranged in front of the scintillator layer 2 in the direction of the X-radiation. The scintillator layer 2 and the a-Si plate 3 are joined by way of one or more adhesive layers 5.

Further detector components, for example housing, electronics and electrical supply, are not represented in the figures. X-ray quanta 9 incident on the scintillator layer 2 are converted there into light quanta 10 and subsequently converted into electrical charge in the corresponding photodiode 7, where they are stored. After the end of a recording, the stored charge is read out by way of the switching elements 8 and is then available as a raw X-ray image. In order to measure a recording temperature $T_A$, one or more temperature sensors 17 are arranged on the X-ray detector 1, for example on the substrate 4.

Figure 3:
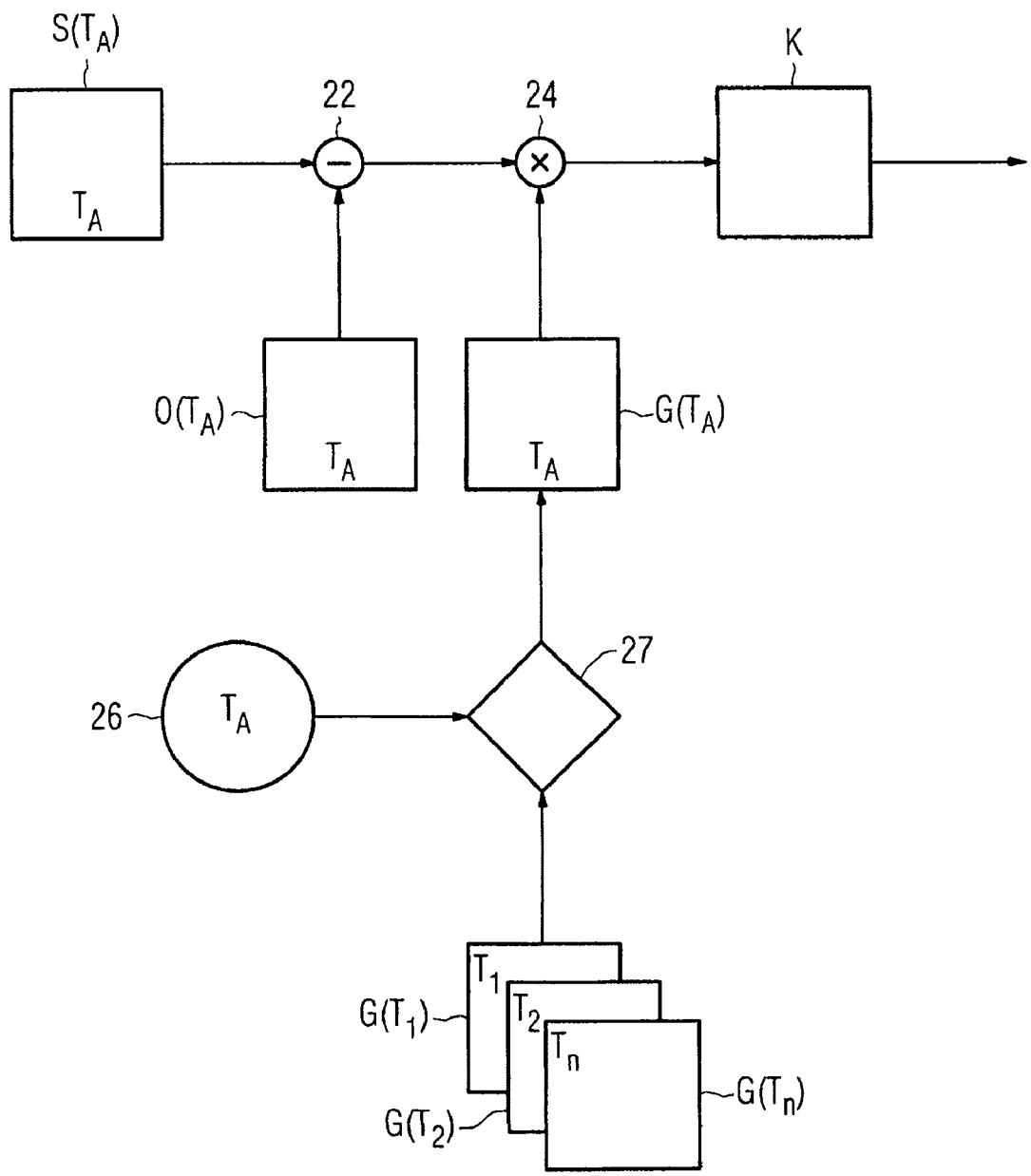
FIG. 3 shows a flow chart of a method according to an embodiment of the invention for generating a corrected X-ray image from a raw X-ray image, wherein a plurality of correction images recorded at temperatures differing from the recording temperature are available.

FIG. 3 shows a flow chart of a method according to an embodiment of the invention for generating a corrected X-ray image K with generation according to an embodiment of the invention of a temperature-adjusted correction image, which is calculated pixel by pixel from a plurality of correction images $G(T_1)$, $G(T_2)$, $G(T_n)$, recorded at temperatures differing from the recording temperature $T_A$. First, a raw X-ray image $S(T_A)$ is recorded and the recording temperature $T_A$ is measured simultaneously, i.e. the temperature at which the X-ray detector 1 is during the recording. For example, the recording temperature $T_A$ is measured by way of the temperature sensor 17.

The raw X-ray image $S(T_A)$ recorded at the recording temperature $T_A$ is subsequently subjected to an offset correction. To this end an offset image $O(T_A)$, compiled at the recording temperature $T_A$ before recording the raw X-ray image, is subtracted from the raw X-ray image $S(T_A)$ by way of electronic subtraction 22. The resulting intermediate image is subsequently subjected to a gain correction, i.e. correction of sensitivity variations. To this end, the resulting intermediate image is corrected by way of electronic multiplication 24 with a temperature-adjusted gain correction image $G(T_A)$. The corrected X-ray image K is obtained as a result.

In order to obtain the temperature-adjusted gain correction image $G(T_A)$, the temperature-adjusted gain correction image $G(T_A)$ has been calculated by way of numerical calculation from a first gain correction image $G(T_1)$, a second gain correction image $G(T_2)$ and a further gain correction image $G(T_n)$ before the gain correction. Temperature information 26 about the recording temperature $T_A$ is used for this. The first gain correction image $G(T_1)$ was recorded at a first temperature $T_1$, the second gain correction image $G(T_2)$ at a second temperature $T_2$ and the further gain correction image $G(T_n)$ at a further temperature $T_n$, for example as part of a final detector check during first use of the X-ray detector.

Figure 4:
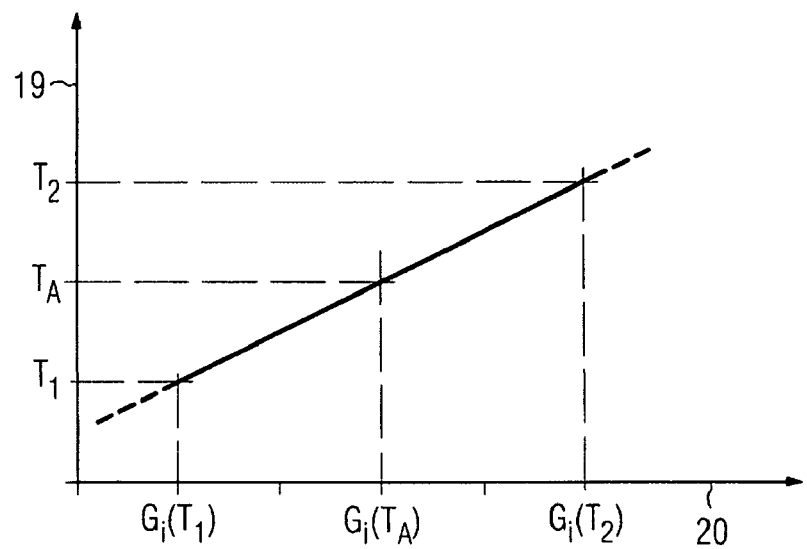
FIG. 4 shows an interpolation method for generating a gain value temperature-adjusted to a recording temperature from two gain values recorded at differing temperatures.

The calculation of the temperature-adjusted gain correction image $G(T_A)$ may, for example, be carried out by means of interpolation when the first temperature $T_1$ lies below the recording temperature and the second temperature $T_2$ lies above the recording temperature $T_A$. FIG. 4 shows a linear interpolation method, the temperature axis 19 being plotted against a gain value axis 20. For each pixel evaluation element i, a temperature-adjusted gain value $G_i(T_A)$ is interpolated linearly from a first gain value $G_i(T_1)$ and a second gain value $G_i(T_2)$ according to the formula $$G_i(T_A) = \frac{(T_A - T_1)}{(T_2 - T_1)} \cdot G_i(T_2) + \frac{T_2 - T_A}{T_2 - T_1} \cdot G_i(T_1).$$

It is nevertheless also possible to use other conventional interpolation methods.

According to another configuration of an embodiment of the invention, the temperature-adjusted correction image is generated by extrapolation. This is appropriate, for example, when the recording temperature $T_A$ lies above or below all temperatures for which there are correction images. To this end, for example, a curve may be fitted by interpolation from the first temperature $T_1$ and the second temperature $T_2$ and this may then be extrapolated as far as the recording temperature $T_A$. Such numerical calculations, e.g. interpolation or extrapolation, are suitable for cases in which at least two correction images, recorded at different temperatures, are available. Naturally, it is likewise possible to use other approximation methods for the numerical calculation.

The situation may arise that only a single first correction image $G(T_1)$ is available, which was recorded at a first temperature $T_1$. For such a case, interpolation or extrapolation is not possible. One configuration of an embodiment of the invention is in this case based on the idea that the effect of temperature leads to local variations, for example of the adhesive layers 5 between the scintillator layer 2 and the a-Si plate 3 or even of the scintillator layer 2 or the a-Si plate 3 per se. These local variations may, for example, be caused by particle inclusions, thickness variations or air bubbles.

Figure 6:
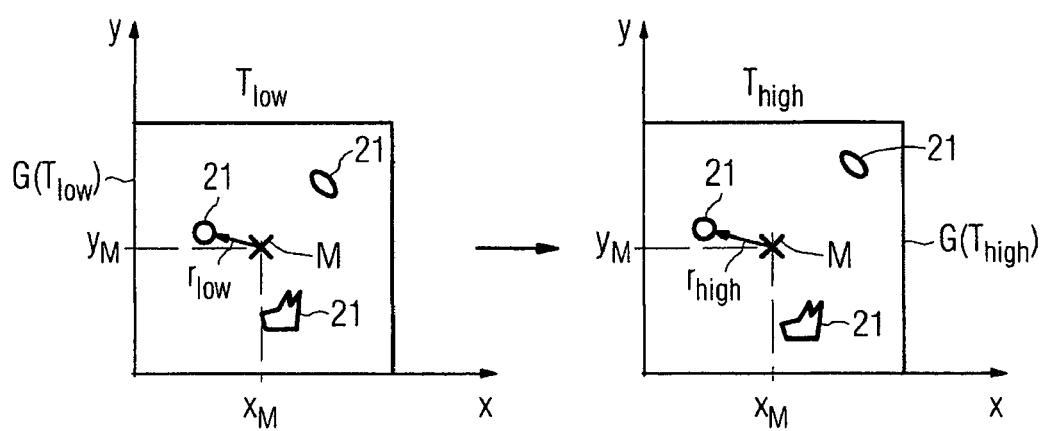
FIG. 6 shows a representation of a gain correction image with particle inclusions revealed, at a low temperature and at a high temperature.

FIG. 6 schematically shows a gain correction image $G(T_{low})$ recorded at a low temperature $T_{low}$ and a gain correction image $G(T_{hgh})$ recorded at a high temperature $T_{hgh}$ in comparison, both of which reveal particle inclusions 21 for example of the adhesive layer 5. The particle inclusions lie in different positions $T_{low}$ at the low temperature than at the high temperature $T_{hgh}$. In general, such local variations can be described by the expansion of the X-ray detector 1 or individual components of the X-ray detector 1, such as the scintillator layer 2 or the a-Si plate 3.

To this end, for example, it may be assumed that the scintillator layer 2 and the substrate 4 expand axisymmetrically with respect to the center M of the respective a-Si plate 3 as the temperature increases. If the active matrix of the X-ray detector includes a single a-Si plate 3, or more generally of a single detector plate, then this generally implies axial symmetry with respect to the center of the a-Si plate 3. The distance $r_{low}$, at which the particle inclusions lie from the center M at a low temperature $T_{low}$, is much less than the distance $r_{hgh}$, at which the particle inclusions lie from the center M at a high temperature $T_{hgh}$. This also includes that the expansion at the center M is zero and maximal at the edge of the a-Si plate 3.

Figure 5:
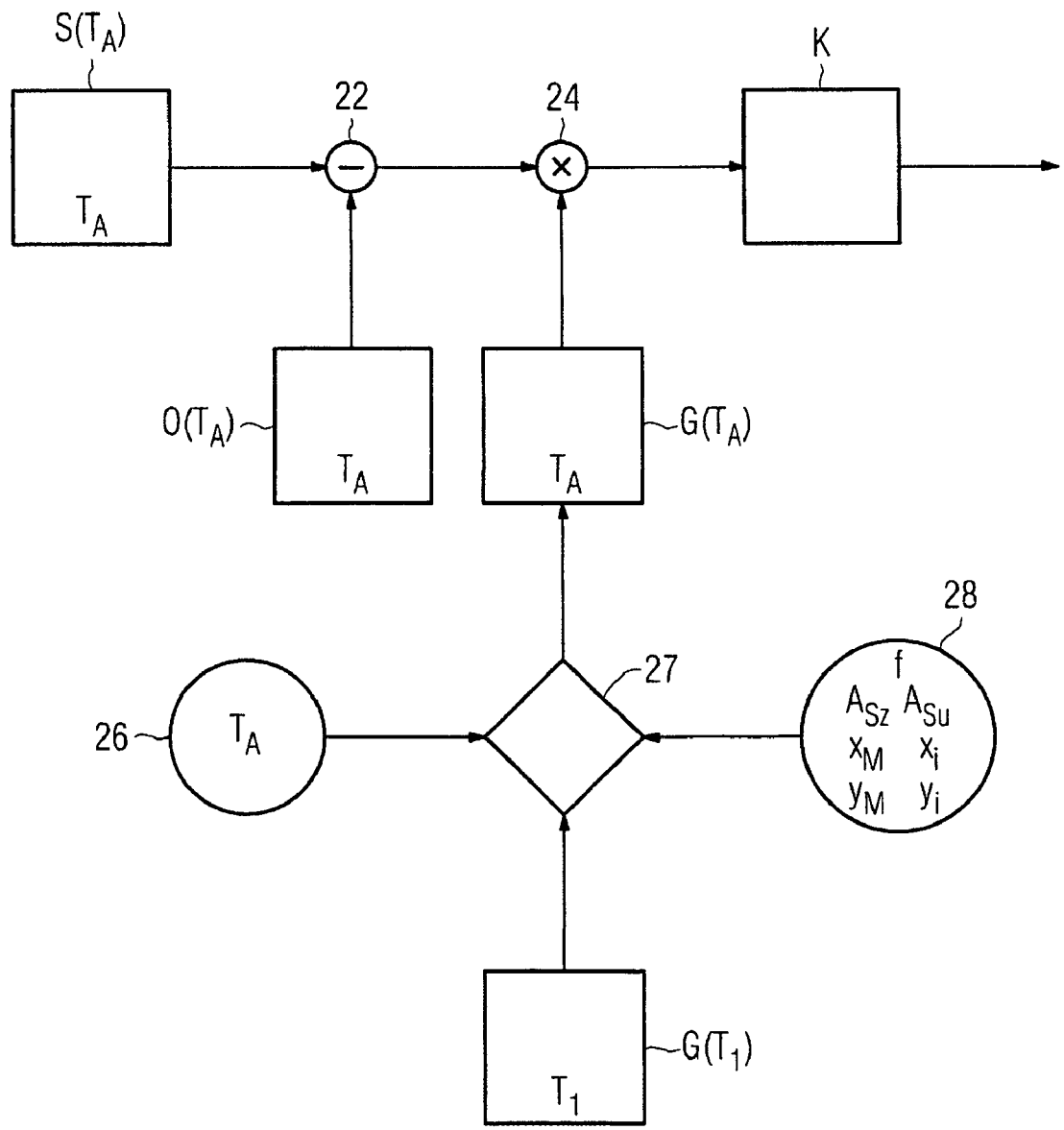
FIG. 5 shows another flow chart of a method according to an embodiment of the invention for generating a corrected X-ray image from a raw X-ray image, wherein only one correction image recorded at a temperature differing from the recording temperature is available.

FIG. 5 shows a flow chart of a method according to an embodiment of the invention for generating a corrected X-ray image K, wherein only a single correction image G(T1) recorded at a first temperature T1 differing from the recording temperature $T_A$ is available. The temperature-adjusted gain correction image $G(T_A)$ is determined from the correction image $G(T_A)$, recorded at the first temperature T1, by taking into account a temperature-induced volume change, in particular an expansion, of subcomponents of the X-ray detector 1.

For instance, the following relationship may be used for the numerical calculation:

$$G_i(T_A)=G_i(T_1) \cdot f(A_{Sz}, A_{Su}, T_A-T_1, \mathrm{sqrt}(x_i-x_i-x_M, y_i-y_M)).$$

where $A_{Sz}$ is the expansion coefficient of the scintillator layer and $A_{Su}$ is the expansion coefficient of the substrate, $x_i$ and $y_i$ are the positions of the $i^{th}$ pixel readout element, $x_m$ and $y_m$ are the positions of the center M and f describes for example stretching or contraction of the correction image in its image plane with the center M, the extension being zero at the center M and maximal at the outer edges of the a-Si plate 3.

According to another variant of the model described in FIG. 5, further expansion coefficients of other components of the X-ray detector 1 or other physical properties of the X-ray detector 1 may also be incorporated. If the active matrix of the X-ray detector 1 is composed of more than one a-Si plate 3 or more than one detector plate, i.e. for example of four abutting a-Si plates 3, then a corresponding axisymmetric volume expansion with respect to the center of each a-Si plate 3 should respectively be taken into account.

Temperature-adjusted correction images already generated numerically may also be used as a basis for further temperature-adjusted correction images to be calculated numerically.

According to one configuration of an embodiment of the invention in the event that correction images are already available, which were recorded previously at a temperature equal or at least similar to the recording temperature $T_A$ or have been generated by way of a calibration method, numerical calculation of a temperature-adjusted correction image may be obviated; instead, the correction images already available are then used for electronically correcting the raw X-ray image.

Figure 7:
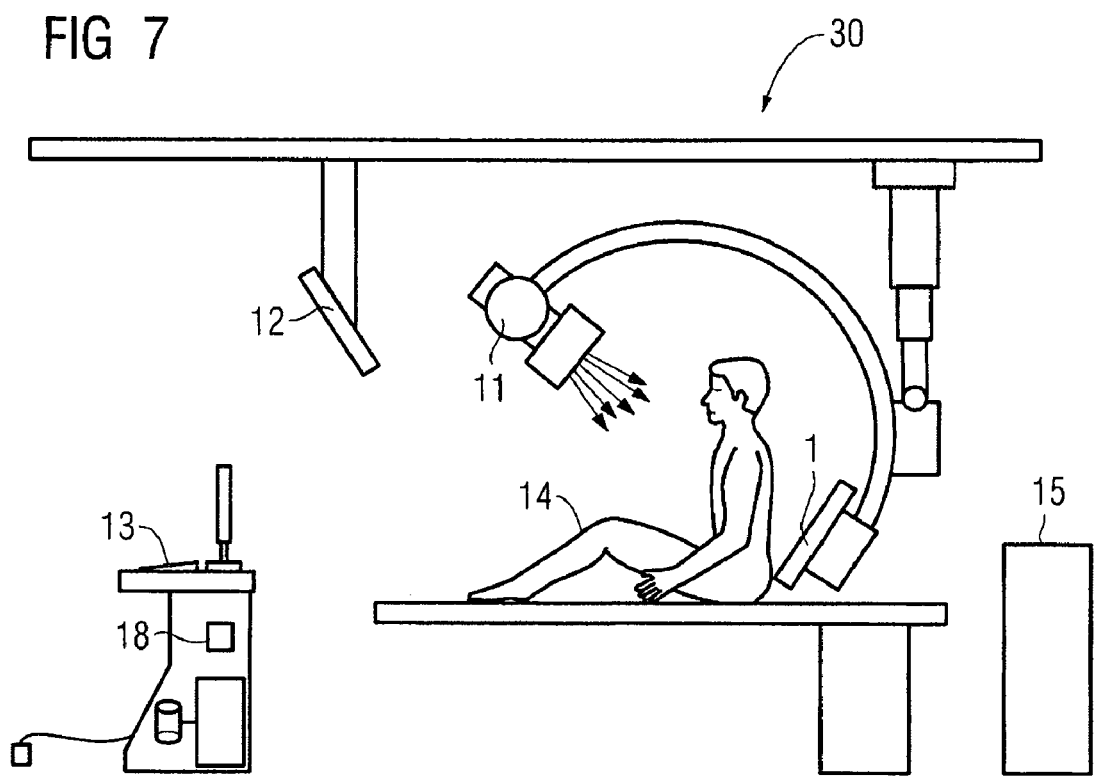
FIG. 7 shows an X-ray system according to an embodiment of the invention having an X-ray detector and an image processing unit, which is contained in a control device and is used for the correction.

FIG. 7 shows by way of example an X-ray system which contains an X-ray detector 1 and a correction unit 18 for carrying out a method according to an embodiment of the invention. The X-ray system furthermore contains an X-ray source 11, a control device 13 in which an image processing unit 18 is integrated, a monitor display 12 and a generator 15. The image processing unit 18 may also be arranged at another position; for example, it may be integrated directly into the X-ray detector 1. A patient 14 is exposed to the X-radiation 11 emitted by the X-ray source 11; the X-radiation is converted into a raw X-ray image by the X-ray detector 1 and the information data are transmitted to the control device 13, for example by means of a wireless radio link. The correction according to an embodiment of the invention as described in the invention is carried out in the image processing unit 18, for example the flat field correction described in FIG. 3 or FIG. 5. The corrected image data may subsequently be post-processed.

At least one embodiment of the invention may be summarized in the following way: For improved temperature-dependent correction, a method is provided for compiling a temperature-adjusted correction image for the electronic correction of a raw X-ray image $S(T_A)$ recorded by an X-ray detector at a recording temperature $T_A$, wherein the temperature-adjusted correction image, in particular the gain correction image $G(T_A)$ temperature-adjusted to the recording temperature $T_A$, is generated by numerical calculation from at least one correction image which was recorded at a temperature differing from the recording temperature $T_A$. In the event of a difference between the recording temperature $T_A$ and the temperature or temperatures for which recorded correction images are available, the raw X-ray image $S(T_A)$ is corrected electronically by way of the temperature-adjusted correction image.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a temperature-adjusted correction image for electronic correction of a raw X-ray image recorded using an X-ray detector at a recording temperature, the method comprising:
    generating the temperature-adjusted correction image by numerical calculation from at least one correction image which was recorded at a temperature differing from the recording temperature, while at least one of incorporating a physical property of the X-ray detector and incorporating a physical property of parts of the X-ray detector.

2. The method as claimed in claim 1, wherein the temperature-adjusted correction image is generated from at least two correction images recorded at different temperatures.

3. The method as claimed in claim 2, wherein the temperature-adjusted correction image is generated from a correction image recorded at a temperature lying above the recording temperature and a correction image recorded at a temperature lying below the recording temperature.

4. The method as claimed in claim 3, wherein the temperature-adjusted correction image is generated by interpolation.

5. The method as claimed in claim 4, wherein the interpolation is linear interpolation.

6. The method as claimed in claim 2, wherein the temperature-adjusted correction image is generated by extrapolation.

7. The method as claimed in claim 6, wherein the extrapolation is linear extrapolation.

8. The method as claimed in claim 1, wherein the temperature-adjusted correction image is generated by numerical calculation from at least one correction image which was recorded at a temperature differing from the recording temperature, while at least one of taking into account a temperature-induced volume change of the X-ray detector and taking into account a temperature-induced volume change of subcomponents of the X-ray detector.

9. The method as claimed in claim 8, wherein the volume change is assumed to be axisymmetric with respect to the center of a detector plate of the X-ray detector.

10. The method as claimed in claim 9, wherein the detector plate is an a-Si plate of the X-ray detector.

11. The method as claimed in claim 1, wherein physical coefficients of at least one of the X-ray detector and subcomponents of the X-ray detector are used.

12. The method as claimed in claim 11, wherein the expansion coefficients of a scintillator layer and of a substrate material of the X-ray detector are used.

13. The method as claimed in claim 11, wherein the physical coefficients are expansion coefficients.

14. A correction method for raw X-ray images recorded at a recording temperature, comprising:
carrying out an electronic correction with a temperature-adjusted correction image generated as claimed in claim 1.

15. A method for generating a corrected X-ray image, comprising: recording a raw X-ray image using an X-ray detector;
measuring a recording temperature of the X-ray detector;
generating, in the event of a substantial difference between the recording temperature and at least one of a temperature and temperatures for which correction images are available, via the method as claimed in claim 1; and
correcting the raw X-ray image electronically by use of the temperature-adjusted correction image.

16. An X-ray system comprising:
an X-ray detector, including at least one temperature sensor, to record a raw X-ray image at a recording temperature; and
an image processing unit to generate a temperature-adjusted correction image by numerical calculation from at least one correction image recorded at a temperature differing from the recording temperature, while at least one of incorporating a physical property of the X-ray detector and incorporating a physical property of parts of the X-ray detector, and to correct the raw X-ray image electronically with the temperature-adjusted correction image.

17. A method, comprising:
recording an X-ray image at a recording temperature; and
generating a temperature-adjusted correction image by numerical calculation from at least one correction image, recorded at a temperature differing from the recording temperature, while at least one of incorporating a physical property of the X-ray detector and incorporating a physical property of parts of the X-ray detector.

18. The method as claimed in claim 17, wherein the temperature-adjusted correction image is generated from at least two correction images recorded at different temperatures.

19. The method as claimed in claim 18, wherein the temperature-adjusted correction image is generated from a correction image recorded at a temperature lying above the recording temperature and a correction image recorded at a temperature lying below the recording temperature.

20. A correction method for raw X-ray images recorded at a recording temperature, comprising:
carrying out an electronic correction with a temperature-adjusted correction image generated as claimed in claim 17.

21. An X-ray system comprising:
means for recording a raw X-ray image at a recording temperature; and
means for generating a temperature-adjusted correction image by numerical calculation from at least one correction image recorded at a temperature differing from the recording temperature, while at least one of incorporating a physical property of the X-ray detector and incorporating a physical property of parts of the X-ray detector, and for correcting the raw X-ray image electronically with the temperature-adjusted correction image.

* * * * *